(12) United States Patent
Yeo et al.

(10) Patent No.: US 9,883,935 B2
(45) Date of Patent: Feb. 6, 2018

(54) PROCESS FOR PREPARING HERNIA MESH FROM MONOFILAMENT

(71) Applicant: SAMYANG BIOPHARMACEUTICALS CORPORATION, Seoul (KR)

(72) Inventors: Guw-dong Yeo, Daejeon (KR); Jun-Bae Kim, Seoul (KR); Jae-Hong Lee, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 278 days.

(21) Appl. No.: 14/849,931

(22) Filed: Sep. 10, 2015

(65) Prior Publication Data

US 2015/0374476 A1    Dec. 31, 2015

Related U.S. Application Data

(62) Division of application No. 11/568,251, filed as application No. PCT/KR2005/004455 on Dec. 22, 2005, now abandoned.

(30) Foreign Application Priority Data

Dec. 29, 2004   (KR) .................. 10-2004-0115443

(51) Int. Cl.
   *A61F 2/00*     (2006.01)
   *D01D 5/12*    (2006.01)
   (Continued)

(52) U.S. Cl.
   CPC .......... *A61F 2/0063* (2013.01); *A61L 31/041* (2013.01); *A61L 31/148* (2013.01);
   (Continued)

(58) Field of Classification Search
   CPC ............ A61F 2/0063; A61F 2230/0017; A61F 2230/0021; D01D 5/08; D01D 5/088;
   (Continued)

(56) References Cited

U.S. PATENT DOCUMENTS

4,769,038 A * 9/1988 Bendavid .............. A61F 2/0063
                                                                606/151
5,218,087 A * 6/1993 Suzuki .................... A61L 17/12
                                                                528/354
(Continued)

*Primary Examiner* — Leo B Tentoni
(74) *Attorney, Agent, or Firm* — Lex IP Meister, PLLC.

(57) ABSTRACT

The present invention relates to a monofilament with a segmented pie structure formed by conjugated spinning of degradable polymers and non-degradable polymers, a hernia mesh having improved flexibility and biocompatibility, and a preparation method of the monofilament. More specifically, the hernia mesh of the present invention having improved flexibility and biocompatibility is prepared using the monofilament obtained by conjugated spinning of degradable polymers and non-degradable polymers into a segmented pie form, to control it to be gradually degraded in the body, whereby the stiffness of the early stage is removed, and thereby the foreign body sensation is also removed.

13 Claims, 4 Drawing Sheets

(51) Int. Cl.

| | | |
|---|---|---|
| D02J 1/22 | (2006.01) | |
| D02G 3/44 | (2006.01) | |
| D01D 5/088 | (2006.01) | |
| D01D 5/16 | (2006.01) | |
| D01D 5/32 | (2006.01) | |
| D01D 10/02 | (2006.01) | |
| A61L 31/14 | (2006.01) | |
| D04B 21/12 | (2006.01) | |
| B29C 47/00 | (2006.01) | |
| B29C 47/30 | (2006.01) | |
| B29C 47/92 | (2006.01) | |
| A61L 31/04 | (2006.01) | |
| D01D 5/08 | (2006.01) | |
| D01D 10/00 | (2006.01) | |
| D03D 7/00 | (2006.01) | |
| D04B 1/22 | (2006.01) | |
| D01D 5/30 | (2006.01) | |
| B29K 23/00 | (2006.01) | |
| B29K 67/00 | (2006.01) | |
| B29L 28/00 | (2006.01) | |
| B29L 31/00 | (2006.01) | |

(52) U.S. Cl.
CPC ...... *B29C 47/0014* (2013.01); *B29C 47/0057* (2013.01); *B29C 47/30* (2013.01); *B29C 47/92* (2013.01); *D01D 5/08* (2013.01); *D01D 5/088* (2013.01); *D01D 5/0885* (2013.01); *D01D 5/12* (2013.01); *D01D 5/16* (2013.01); *D01D 5/30* (2013.01); *D01D 5/32* (2013.01); *D01D 10/00* (2013.01); *D01D 10/02* (2013.01); *D02G 3/448* (2013.01); *D02J 1/22* (2013.01); *D02J 1/228* (2013.01); *D02J 1/229* (2013.01); *D03D 7/00* (2013.01); *D04B 1/22* (2013.01); *D04B 21/12* (2013.01); *A61F 2002/0068* (2013.01); *A61F 2250/0031* (2013.01); *B29C 2947/92695* (2013.01); *B29K 2023/12* (2013.01); *B29K 2067/04* (2013.01); *B29K 2995/0037* (2013.01); *B29L 2028/00* (2013.01); *B29L 2031/7546* (2013.01)

(58) Field of Classification Search
CPC .......... D01D 5/0885; D01D 5/12; D01D 5/16; D01D 5/32; D01D 10/02; D01F 8/04; D01F 8/06; D01F 8/08; D01F 8/12; D01F 8/14; D01F 8/16; D02G 3/448; D02J 1/22; D02J 1/228; D02J 1/229; D04B 21/00; D04B 21/12; D10B 2509/08
USPC .......... 264/78, 103, 172.14, 172.17, 172.18, 264/178 F, 178 R, 210.7, 210.8, 211.14, 264/211.15, 211.17, 236, 342 RE; 8/494, 8/497; 28/151, 169, 190; 66/195
See application file for complete search history.

(56) References Cited

U.S. PATENT DOCUMENTS

| | | | | |
|---|---|---|---|---|
| 5,569,273 | A * | 10/1996 | Titone | A61F 2/0063 442/1 |
| 5,593,778 | A * | 1/1997 | Kondo | D01F 8/14 264/239 |
| 6,287,316 | B1 * | 9/2001 | Agarwal | A61F 2/0063 66/195 X |
| 6,624,097 | B2 * | 9/2003 | Martin | D01F 8/04 428/373 |
| 2002/0106509 | A1 * | 8/2002 | Figuly | D01F 8/04 428/364 |
| 2003/0175513 | A1 * | 9/2003 | Tokarsky | D01D 5/08 428/364 |
| 2005/0010306 | A1 * | 1/2005 | Priewe | A61F 2/0063 623/23.76 |

* cited by examiner

PROCESS FOR PREPARING HERNIA MESH FROM MONOFILAMENT

CROSS-REFERENCES TO RELATED APPLICATION

This application is a Divisional Application of now abandoned U.S. patent application Ser. No. 11/568,251 filed on Oct. 24, 2006, which is a National Stage application of PCT/KR05/04455 filed on Dec. 22, 2005, which claims priority to Korean Patent Application No. KR 10-2004-015443 filed on Dec. 29, 2004, the contents of which are incorporated herein by reference.

BACKGROUND OF THE INVENTION (a) Field of the Invention

The present invention relates to a monofilament having a segmented pie structure formed by conjugated spinning of degradable polymers and non-degradable polymers, a hernia mesh comprising the monofilament having improved flexibility and biocompatibility, and a method for preparing the same. More specifically, the present invention relates to a monofilament prepared by conjugated spinning of degradable polymers and non-degradable polymers in the form of a segmented pie; a hernia mesh that is prepared with the monofilament and that is controlled to be gradually degraded in the body while losing the stiffness of the early stage, causing no misfeelings, and having improved flexibility and biocompatibility; and a method of preparation thereof.

(b) Description of the Related Art

Tension-free hernioplasty (Lichtenstein I L, Am J Surg 1989; 157; 188-193) is considered to be a useful method for reparation of hernias, because the relapse ratio thereafter is low, the operative time is short, and the operative wound heals quickly, and thereby the patient can rapidly return to normal life. Conventionally, since the mesh used for hernia repair is required to have the capability of maintaining its chemical and physical properties for several years to strengthen the peritoneum, polypropylene monofilaments have been used as the material for a hernia mesh. However, it has been reported that the polypropylene mesh may have the potential to generate fistulas in the intestine (Seelig M H, "A rare complication after incisional hernia repair". Chirurg 1995; 66(7); 739-741, Leber G E, "Long-term complications associated with prosthetic repair of incisional hernias", Arch Surg 1988; 133(4); 378-382). Further, as general side effects of the polypropylene mesh, an edema, a restriction of abdominal wall mobility due to stiffness of the peritoneum where the artificial membrane is located and pain from misfeelings caused by the stiffness, a chronic inflammatory response between the polypropylene fibers and tissues in body, and the like have been reported (Amid P K, "Biomaterials for abdominal wall hernia surgery and principles of their applications", Lagenbecks Arch Chir 1994; 379(3): 168-171, Waldrep D J, "Mature fibrous cyst formation after Marlex Vestweber K, Results of recurrent abdominal wall hernia repair using polypropylene mesh". Zentralblatt Für Chirurgie 1997; 122:885-8, Belton J M, "Integration of biomaterials implanted into abdominal wall: mesh ventral herniorrhaphy: a newly described pathologic entity". Am Surg 1993; 59(11):716-8, "Process of scar formation and macrophage response". Biomaterials 1995; 16(5):381-7, Klinge U, "Changes in abdominal wall mechanics after mesh implantation". Experimental changes in mesh stability. Lagenbecks Arch Chir 1996; 381(6): 323-32).

The hernia mesh needs stiffness in order to be positioned and fixed on the surgical wound region when performing the surgical operation. For that purpose, several methods to prepare the hernia mesh using fibers in the monofilament form have been known. U.S. Pat. No. 4,347,847, U.S. Pat. No. 4,452,245, U.S. Pat. No. 5,569,273, and U.S. Pat. No. 6,287,316 disclose a method to prepare a hernia mesh consisting of polypropylene monofilaments. However, since polypropylene is non-degradable, after performing the surgical operation using the hernia mesh, the strength and stiffness of the mesh that are necessary during the initial stage after the surgical operation are continuously maintained in the body. Therefore, the mesh has excessive stiffness even after the wound has healed, causing pain to the patient due to misfeelings. Further, U.S. Pat. No. 5,292,328 discloses a method of preparing a hernia mesh consisting of polypropylene multifilaments in order to improve the flexibility, in which the mesh has a somewhat improved initial flexibility compared with that consisting of the monofilaments. However, since the mesh consists of only non-degradable materials, there are also some problems in that the initial strength and stiffness of the mesh are continuously maintained in the body, and an excessive amount of polypropylene remains in the body.

To solve these problems, studies on development of a partially degradable mesh wherein the content of polypropylene is decreased and the strength and stiffness necessary for the initial stage is supplemented by additionally comprising degradable materials, have been disclosed in U.S. Pat. No. 4,652,264 and U.S. Pat. No. 6,162,962. Herein, the degradable materials are partially degraded after the wound has healed, to improve the flexibility of the mesh. U.S. Pat. No. 4,652,264 discloses a method to prepare a mesh by combining threads consisting of three different materials, of which two are degradable and one is non-degradable. U.S. Pat. No. 6,287,316 discloses a method of preparing a mesh using a multifilament consisting of degradable materials and non-degradable materials. However, since the meshes prepared by the above methods consist of several threads of degradable and non-degradable materials in the combined form, there is a possibility of bacterial infection within the spaces between the threads, which is an inherent defect of multifilaments. Further, since the methods employ the multifilament form wherein several strands of fiber are combined, the amount of materials required for exhibiting the necessary stiffness is larger than the case of using the monofilament. In addition, the multifilament causes a strong foreign body response due to the large surface area (Beets G L, "Foreign body reactions to monofilament and braided polypropylene mesh used as preperitoneal implants in pigs". Eur J Surg 1996; 162:823-825).

As known from the above prior art, although the use of a hernia mesh has been regarded as a basic means in performing hernia repairs, there are unsatisfactory results obtained from the studies to develop a hernia mesh for improving the convenience in performing the operation, reducing the misfeelings, and having improved biocompatibility. Therefore, it is required to develop a hernia mesh that can maintain its strength and stiffness at the early stage, thereby ensuring convenience in performing the operation, and be partially degraded as the surgical wound is healed, thereby improving the flexibility of the remaining mesh.

SUMMARY OF THE INVENTION

The object of the present invention is to provide a monofilament having a segmented pie structure formed by conjugated spinning of degradable polymers and non-degradable polymers.

Another object of the present invention is to provide a hernia surgical mesh comprising the monofilament, having improved flexibility and biocompatibility.

Another object of the present invention is to provide a method of preparing the hernia mesh.

DETAILED DESCRIPTION OF THE PREFERRED EMBODIMENTS

The present inventors have conducted continued studies to develop a novel hernia mesh with partial degradability, which maintains its strength and stiffness at the early stage to secure convenience in performing a surgical operation and then becomes partially degraded during healing of the surgical wound to increase the flexibility of the mesh remaining in the body, resulting in alleviating the patient's pain and improving the biocompatibility by remarkably reducing the amount of non-degradable materials used. As the result, the present inventors found that when preparing a monofilament in the segmented pie form by conjugated spinning of degradable polymers and non-degradable polymers, the strength and stiffness necessary for the early stage of the surgical operation can be achieved by the stiffness characteristic of the monofilament itself, and after performing the operation, the monofilament becomes partially degraded in the body, and thereby the mesh consisting thereof can remain in the body in the more flexible structure, to complete the present invention.

Hereinafter, the present invention will be described in detail.

The present invention relates to a hernia mesh with improved flexibility and biocompatibility and a preparation method thereof, wherein the mesh comprises monofilaments having the segmented pie structure formed by conjugated spinning of degradable polymers and non-degradable polymers, being controlled to be gradually degraded in the body, to remove the initial stiffness of the mesh and to avoid misfeelings due to the remaining mesh.

Figure 1A:
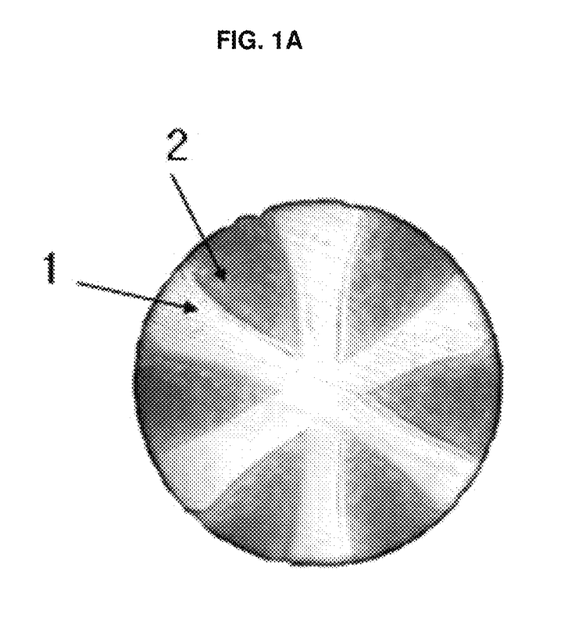
FIG. 1A is an optical microscopic image of a cross section of the conjugated filament in the segmented pie form according to the present invention [1: degradable polymer, 2: non-degradable polymer].
Figure 1B:
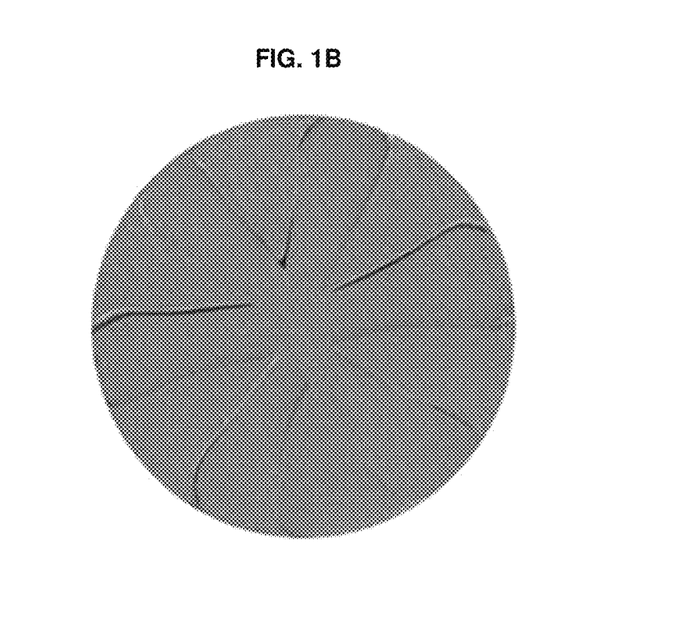
FIG. 1B is a SEM (scanning electron microscope) image of the cross section of the conjugated filament in the segmented pie form according to the present invention.

The monofilament in the segmented pie form, which composes the hernia mesh of the present invention, consists of a degradable polymer and a non-degradable polymer, wherein the non-degradable polymer (2) is separated into several partitions by the degradable polymer (1), and the degradable polymer (1) has a continuous form [see FIG. 1A]. The monofilament in the segmented pie form of the present invention is present in the monofilament form before degradation, and then, as the degradable polymer becomes degraded, the monofilament is divided into individual strands as a multifilament form, to exhibit improved flexibility.

The degradable polymer used in the present invention may be a homopolymer or a copolymer comprising one or more selected from the group consisting of glycolide, glycolic acid, lactide, lactic acid, caprolactone ($\epsilon$-caprolactone), dioxanone (p-dioxanone), trimethylenecarbonate, polyanhydride, and polyhydroxyalkanoate, and is more preferably a glycolide/caprolactone copolymer or a dioxanone/trimethylenecarbonate/caprolactone copolymer.

The non-degradable polymer used in the present invention may be selected from the group consisting of polyolefins such as polypropylene, polyethylene, and a copolymer of propylene and ethylene; polyamides such as nylon 6 and nylon 66; polyurethanes; and fluoropolymers such as polyvinylidene fluoride, and is more preferably polypropylene or a copolymer of propylene and ethylene.

Figure 3A:
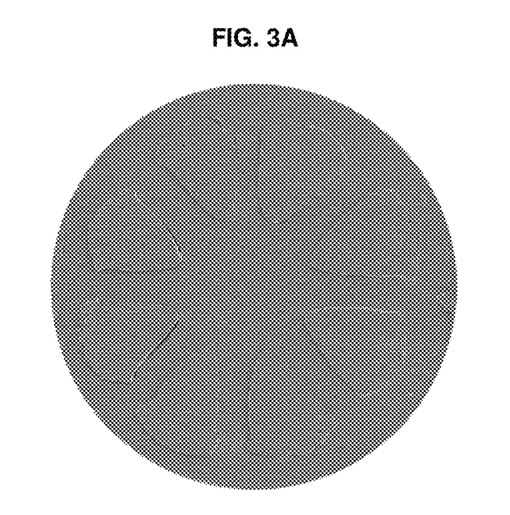
FIG. 3A is a SEM image of the cross section of the monofilament prepared by conjugated spinning using 75 volume % of degradable materials.

In particular, the content of the degradable polymer is preferably 30 to 70 vol % and the content of the non-degradable polymer is preferably 30 to 70 vol %, and more preferably, the content of the degradable polymer is 40 to 60 vol % and the content of the non-degradable polymer is 40 to 60 vol %. When the content of the degradable polymer is less than 30 vol %, in spinning, the volume of the degradable polymer is too small to separate the non-degradable polymer, and thus the non-degradable polymer is in the continuously linked form. When the content of the non-degradable polymer is less than 30 vol %, the remaining amount of the non-degradable polymer after degradation is too low to maintain minimum strength, and further, the monofilament may be prepared in a sea/islands type wherein the non-degradable polymer is surrounded by the degradable polymer as shown in FIG. 3A.

The monofilament prepared by conjugated spinning may be divided into several types, such as sea/islands type, a segmented pie type, a side-by-side type, a sheath/core type, and the like, depending on the structures, and the preferable type in the present invention is the segmented pie type. The segmented pie type has some advantages in that the degradable materials and the non-degradable materials are uniformly spread on the surface of the fibers to attain the mobility of the peritoneum by an appropriate combination of fat tissue formed around the degradable material and connective tissue appeared around the non-degradable material, and to improve the adhesive property between the mesh and the tissues. Further, different from the conjugated yarn type such as the sea/islands type or the sheath/core type whereon the non-degradable material is surrounded by the degradable material, the segmented pie type monofilament can connect with the tissues in the body at the early stage after the surgical operation, and thus induce strong adhesion between the mesh and the tissues shortly after performing the surgical operation [U. Klinge, "Influence of polyglactin-coating on functional and morphological parameters of polypropylene-mesh modifications for abdominal wall repair", Biomaterials 1999; 20:613-623, U. Klinge, "Foreign body reaction to meshes used for the repair of abdominal wall" Hernias, Eur J Surg, 1999; 165:665-673].

In mesh prepared with the segmented pie type monofilament, in order to reduce the stiffness after healing of the surgical wound to less than 70% of the initial stiffness and to improve the flexibility of the mesh, it is preferable to divide the non-degradable polymer into at least four strands, and more preferably 6 to 10 strands.

In mesh prepared with the sea/islands type or sheath/core type of monofilament, the sea or sheath which is an outside component of the monofilament must be composed of the degradable polymer, and the island or core which is an inside component of the monofilament must be composed of the non-degradable polymer. In these cases, as the degradable polymer located at the outside of the monofilament is degraded and dispersed, the monofilament starts exhibiting an excessive surface area and excessive fibrosis (capsule formation) occurs, whereby the strong adhesion between the mesh and the tissues in the body is inhibited. Further, in the side-by-side type of monofilament wherein one of two components is located at one side of the cross section and the other is located at the other side, the non-degradable polymer causes an inflammatory response, and rigid connective tissue is formed around the mesh, inhibiting the mobility of the peritoneum. These types are unsuitable for the object of the present invention which is to improve the flexibility of the peritoneum, and are difficult to prepare with two components having different melting behaviors and different thermal contractibility. In addition, since the two components have the same diameter, the diameter of the remaining non-degradable fiber increases, and thereby there is a limitation in improving the flexibility of the remaining mesh.

The diameter of the monofilament may be controlled so as to have the strength and/or stiffness necessary at the early stage after performing the surgical operation, and at the same time to prevent a large amount of the non-degradable polymer from remaining in the body, thereby improving the biocompatibility and the flexibility. That is, in order to maintain the initial strength and stiffness, it is required for the fiber to have a density and diameter of a certain degree or higher, while in order to minimize a foreign body response when inserted in the body, it is required that the total amount of fibers used is minimized. In the present invention, the diameter of the monofilament is preferably 100 to 250 µm.

The mesh of the present invention may be prepared in various shapes, and is preferably prepared as a net-structure such as a square, hexagonal, or network shape. The density of the mesh is preferably 8 to 20 gauges/inch based on the distance between the needles in a flat warp knitting machine. When the mesh is cut in a suitable size and shape for the surgical wound region of a patient and is applied to the wound region, problems such as material particles or an unraveling phenomenon may occur at the edge of the cut-off mesh. Therefore, a structure that readily generates particles or an unraveling phenomenon when cut may be relatively undesirable, and the net-structure such as the square, hexagonal, or network may be desirable in view of lesser particle generation when cut.

In the present invention, the pore size of the mesh may be 0.1 to 4.0 mm, preferably 2.0 to 3.0 mm, and the thickness of the mesh may be 200 to 800 µm, preferably 500 to 600 µm.

In the hernia mesh of the present invention, it is preferable that the non-degradable polymer is partitioned by the degradable polymer, and that the degradable polymer is continuously linked.

The present invention provides a method of preparing the monofilament in the segmented pie structure formed by conjugated spinning of the degradable polymer and the non-degradable polymer.

Figure 4:
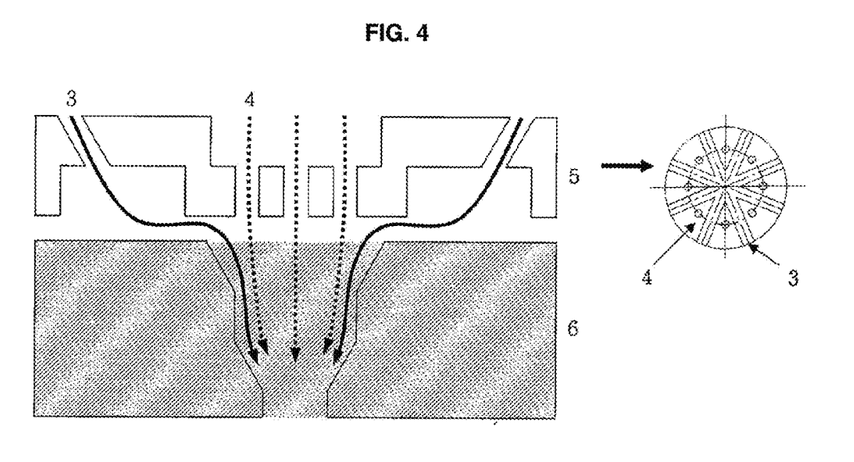
FIG. 4 is a schematic diagram showing the flow of two polymers at a distributing plate and a nozzle in the conjugated spinning apparatus for preparing the monofilament in the segmented pie form.

In the present invention, to perform spinning, any conventional conjugated spinning apparatus may be used. In detail, the polymers are melted by two extruding apparatuses for conjugated spinning. Each of the melted polymers is discharged in a desired amount through each quantitative pump to control the content ratio of each component. The polymers that are melted and passed through the quantitative pump are subjected to conjugated spinning into one strand of fiber through a conjugated spinning block. FIG. 4 is a schematic diagram of the preparation of the monofilament in the segmented pie form, showing the flows of the degradable polymer (3) and the non-degradable polymer (4) in the conjugated spinning block. The melted polymer discharged from each quantitative pump is gathered at the distributing plate (5) in the conjugated spinning block, and passed through the nozzle to prepare the monofilament in the segmented pie form. The strand obtained by conjugated spinning is solidified and crystallized in a cooling bath. The air gap between the spinnerette and the surface of water in the cooing bath is preferably 0.5 to 100 cm, and more preferably 1 to 30 cm. The solidified fiber is drawn through a multi-stage drawing apparatus and wound in a winder in order to obtain an improvement of the property by orientation. A preferable embodiment of the monofilament in the segmented pie form is shown in FIG. 1A.

Figure 3B:
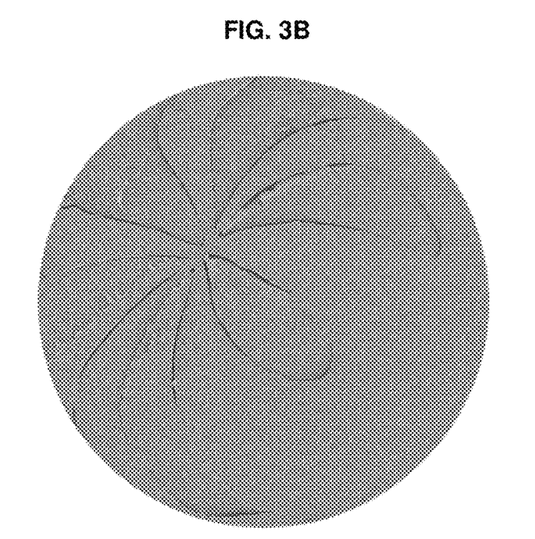
FIG. 3B is a SEM image showing a distortion of the monofilament in the segmented pie form when the difference between the melt indexes is more than 14 in conjugated spinning.

To prepare the uniform and stable monofilament in the segmented pie form by spinning process, the melt indexes (MI) of the two polymers and the spinning conditions have to be exactly controlled. The melt index of the degradable polymer may not be lower than that of the non-degradable polymer to maintain the segmented pie structure, and the difference between the melt indexes of the degradable polymer and the non-degradable polymer is preferably 10 or less. If the melt index of the degradable polymer is lower than that of the non-degradable polymer, the segmented pie structure may be obtained in a distorted and unequal form wherein the distribution of the non-degradable polymer is not equally distributed, being concentrated on a certain position as shown in FIG. 3B. Further, if the difference between the melt indexes of the two polymers is more than 10, phase separation easily occurs. Therefore, it is preferable that the melt index of the degradable polymer is not lower than that of the non-degradable polymer, and that the difference between the melt indexes of the two polymers is 10 or less.

Figure 3C:
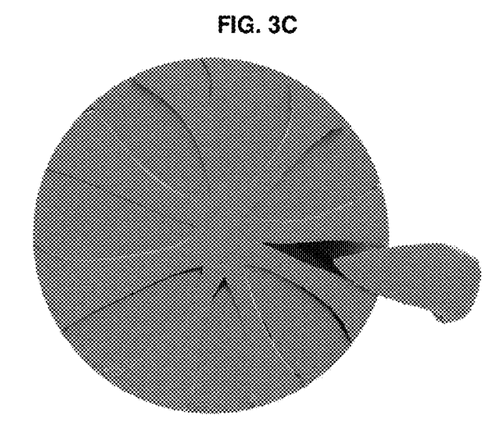
FIG. 3C is an SEM image showing fiber separation when the stress-relaxation is not performed under the drawing conditions in conjugated spinning.

In addition, when the monofilament in the segmented pie form is prepared by conjugated spinning of two polymers having different properties such as the melting point, the degree of crystallinity, the thermal contractibility and the like, improper drawing conditions cause curling and phase separation of the two components as shown in FIG. 3C. To prevent such a curling phenomenon, the spinning temperature is controlled within a certain range so that the melt index of the degradable polymer is the same as or higher than that of the non-degradable polymer, to allow the melting behavior of the two polymers to form the symmetric structure of the segmented pie form. Further, to prevent the fiber phase separation phenomenon, in a final drawing oven, stress relaxation of at least 10% and preferably 10 to 20% is applied in consideration of the thermal contraction rate of the two polymer components to stabilize the structure.

In order to easily distinguish the mesh when performing the surgical operation, the mesh fibers may be dyed at regular intervals. Herein, to prevent the dye from remaining in the body, it is preferable to dye only the degradable polymer part. Any dye that is conventionally employed in preparing sutures, such as D&C violet No. 2, D&C Green No. 6, FD&C Blue No. 2, and the like, may be used.

The present invention also provides a method for preparing a mesh using the above monofilament in the segmented pie form.

In the present invention, the mesh may be prepared through three conventional steps of warping, knitting, and curing.

In the warping step, several strands are regularly wound on a beam with a constant tension to equally supply a regular amount of fiber before the knitting step. Then, the beam is equipped in a flat warp knitting machine to prepare a mesh. In the present invention, the mesh may be prepared by a Tricot flat warp knitting machine or a Raschel flat warp knitting machine. When preparing the mesh, the texture and shape may be controlled so as to give the mesh the necessary strength and stiffness at the early stage and to simultaneously prevent the non-degradable materials from remaining in the body in a large amount to improve the biocompatibility and flexibility, controlling the strength and stiffness of the texture of the mesh. As a final step, the prepared mesh is cured to fix the shape of the mesh. The curing step is performed under temperature and time conditions such that yellowing and a change of the properties are avoided. Conventionally, the mesh is cured at a temperature 10° C. to 15° C. lower than the melting point of the component constituting the mesh, e.g., at 90° C. to 160° C., for 1 to 30 minutes. For example, in preparing the mesh comprising polypropylene, if the melting point of the degradable component is higher than that of polypropylene, the curing temperature of the mesh is determined on the basis of the melting point of polypropylene, that is, the mesh may be cured at 100 to 155° C. for 3 to 20 minutes.

In an embodiment of the present invention, a mesh having the following texture may be used by a flat warp knitting machine.

(The Warp Knitted Texture Example 1)
The number of gauge=18 (Gauges/inch)
    G1=10 01 10 12 21 12
    G2=00 11 00 22 11 22
    G=guide bar
(The Warp Knitted Texture Example 2)
The number of gauge=12 (Gauges/inch)
    G1=10 01 10 12 21 12
    G2=00 11 00 22 11 22
    G3=00 11 00 22 11 22
    G4=00 11 00 11 00 11
(The Warp Knitted Texture Example 3)
The number of gauge=12 (Gauges/inch)
    G1=10 01 10 12 21 12×4
    G2=00 11 00 22 11 22×4
    G3=22 33 22 33 22 33 11 22 11 00 11 11 22 11 33 22 33 22 33 22 44 33 44
    G4=11 22 11 33 22 33 22 33 22 44 33 44 22 33 22 33 22 33 11 22 11 22 00 22
(The Warp Knitted Texture Example 4)
The number of gauge=18 (Gauges/inch)
    G1=10 12 23 21
    G2=23 21 10 12

(The Warp Knitted Texture Example 5)
The number of gauge=18 (Gauges/inch)
    G1=21 12 10 12 21 23
    G2=12 21 23 21 12 10

Figure 2A:
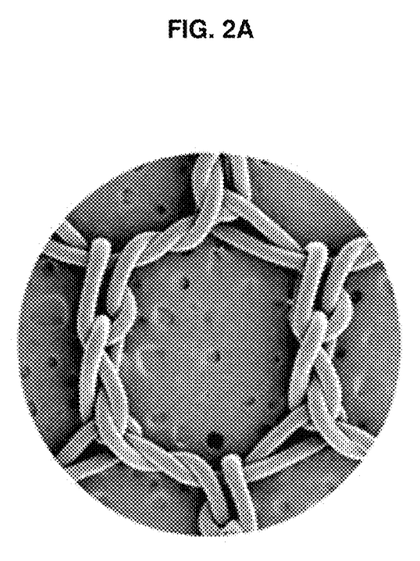
FIG. 2A is a SEM image prior to degradation of the mesh prepared with the monofilament obtained by conjugated spinning.
Figure 2B:
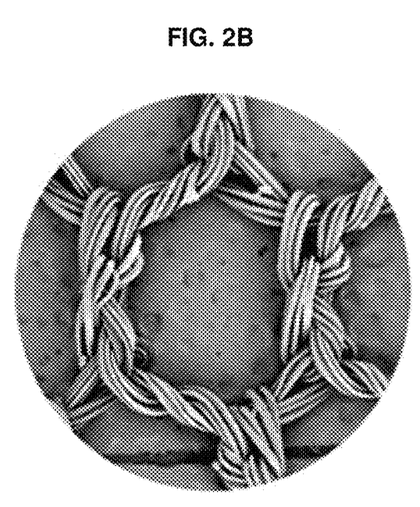
FIG. 2B is a SEM image after degradation of the mesh prepared with the monofilament obtained by conjugated spinning.

FIG. 2A is an electronic microscopy image of the mesh according to the present invention before degradation, and FIG. 2B is that after degradation, showing that the component constituting the mesh has the monofilament form prior to degradation, and is converted to the multifilament form of several strands of the non-degradable polymer after degradation.

In the present invention, the mesh is prepared with the monofilament in the segmented pie form wherein the degradable polymer and the non-degradable polymer are repeatedly and alternatively distributed in all directions throughout the whole fiber, to improve the biocompatibility and the adhesive strength to the tissue in the body at the early stage after performing the surgical operation. Further, the stiffness after degradation is reduced by at least 70% compared with that before degradation, to maximize the flexibility of the mesh remaining in the body after the surgical wound is healed. Compared with the conventional mesh that contains only non-degradable components or partially degradable components, in the present invention the initial and remaining amounts of the non-degradable components in the mesh are lowered, and simultaneously the biocompatibility and the flexibility of the mesh are improved.

Therefore, the mesh according to the present invention is suitable for hernia repair, since the mesh maintains the strength and the stiffness to attain the convenience of the surgical operation at the early stage, and is partially degraded to improve the flexibility as the surgical wound is healed.

According to the present invention, the monofilament with the segmented pie structure formed by conjugated spinning of the degradable polymer and the non-degradable polymer may be applied to not only hernia mesh, but also to other operations, such as vaginal sling procedures, artificial ligament and tendon operations, fascial deficiencies which require the add an reinforcing material or a bridging material, and the like.

Hereinafter, the present invention will be more specifically described by the following examples, which should not be understood to limit the scope of the invention.

Example 1

The monofilament in the segmented pie form was prepared through conjugated spinning of 55 vol % of a glycolide (75)/caprolactone (25) copolymer as a degradable polymer and 45 vol % of polypropylene as a non-degradable polymer under the conditions shown in the following Table 1. The prepared monofilament in the segmented pie form was warped with 150 yarns/7" beam to prepare the mesh according to the above warp knitted texture of Example 1. The prepared mesh was cured at 150° C. for 5 minutes. The properties of the mesh, such as thickness, weight, tensile strength, and stiffness were determined according to the conventional measuring methods, and the results are shown in the following Table 6.

TABLE 1

| | polypropylene | glycolide (75)/caprolactone (25) copolymer |
|---|---|---|
| Polymer | | |
| Melt index (g/10 min, 230° C.) | 10 | 13 |
| Spinning Conditions | | |
| Extruder | Ext. 1 | Ext. 2 |
| The number of segments of the non-degradable polymer | 6 | — |
| Pre-pump pressure (kgf/cm$^2$) | 80 | 80 |
| Temperature in Extruder (° C.)  Zone 1 | 150 | 150 |
| Zone 2 | 160 | 165 |
| Zone 3 | 170 | 180 |
| Zone 4 | 175 | 190 |
| Zone 5 | 175 | 195 |
| Temperature in Manifold (° C.) | 180 | 198 |
| Temperature in Quantitative Pump (° C.) | 180 | 186 |
| Temperature in Nozzle Pack Die (° C.) | | 204 |
| Capacity of Quantitative Pump (cc/rev) | 0.3 | 0.6 |
| Revolution speed of Quantitative Pump (rpm) | 8.75 | 5.35 |
| Temperature in Cooling Bath (° C.) | | 25 |
| Drawing Conditions | | |
| First Roller velocity (m/min) | | 6.7 |
| First Drawing Oven Temperature (° C.) | | 70 |
| Second Roller velocity (m/min) | | 47 |
| Second Drawing Oven Temperature (° C.) | | 100 |
| Third Roller velocity (m/min) | | 55 |
| Third Drawing Oven Temperature (° C.) | | 140 |
| Fourth Roller velocity (m/min) | | 46 |
| Total Drawing Ratio | | 6.86 |
| Preparation Conditions of the Mesh | | |
| Warping Conditions | | 150 yarns/7" beam |
| Warp Knitted Texture | | Warp Knitted Texture Example 1 |
| Curing Conditions | | 150° C., 5 minutes |

Example 2

The monofilament in the segmented pie form was prepared through conjugated spinning of 55 vol % of a glycolide (75)/caprolactone (25) copolymer as a degradable polymer and 45 vol % of a propylene (97)/ethylene (3) copolymer as a non-degradable polymer under the conditions shown in the following Table 2. The prepared monofilament in the segmented pie form was warped with 120 yarns/7" beam to prepare the mesh according to the above warp knitted texture of Example 2. The prepared mesh was cured at 155° C. for 3 minutes. The properties of the mesh, such as thickness, weight, tensile strength, and stiffness were determined according to the conventional measuring methods, and the results are shown in the following Table 6.

TABLE 2

| Polymer | Propylene (97)/ethylene (3) random copolymer | Glycolide (75)/caprolactone (25) copolymer |
|---|---|---|
| Melt index (g/10 min, 230° C.) | 8 | 12 |
| Spinning Conditions | | |
| Extruder | Ext. 1 | Ext. 2 |
| The number of segments of the non-degradable polymer | 6 | — |
| Pre-pump pressure (kgf/cm$^2$) | 80 | 80 |
| Temperature in Extruder (° C.)  Zone 1 | 150 | 150 |
| Zone 2 | 160 | 165 |
| Zone 3 | 165 | 180 |
| Zone 4 | 170 | 190 |
| Zone 5 | 170 | 195 |
| Temperature in Manifold (° C.) | 175 | 198 |
| Temperature in Quantitative Pump (° C.) | 175 | 186 |
| Temperature in Nozzle Pack Die (° C.) | | 203 |
| Capacity of Quantitative Pump (cc/rev) | 0.3 | 0.6 |
| Revolution speed of Quantitative Pump (rpm) | 8.75 | 5.35 |
| Temperature in Cooling Bath (° C.) | | 25 |
| Drawing Conditions | | |
| First Roller velocity (m/min) | | 6.1 |
| First Drawing Oven Temperature (° C.) | | 70 |
| Second Roller velocity (m/min) | | 47 |
| Second Drawing Oven Temperature (° C.) | | 100 |
| Third Roller velocity (m/min) | | 55 |
| Third Drawing Oven Temperature (° C.) | | 140 |
| Fourth Roller velocity (m/min) | | 46 |
| Total Drawing Ratio | | 7.54 |

TABLE 2-continued

| Polymer | Propylene (97)/ ethylene (3) random copolymer | Glycolide (75)/ caprolactone (25) copolymer |
|---|---|---|
| Preparation Conditions of the Mesh | | |
| Warping Conditions | 120 yarns/7" beam | |
| Warp Knitted Texture | Warp Knitted Texture Example 2 | |
| Curing Conditions | 155° C., 3 minutes | |

Example 3

The monofilament in the segmented pie form was prepared through conjugated spinning of 55 vol % of a dioxanone (90)/trimethylenecarbonate (9)/caprolactone (1) tri-block copolymer as a degradable polymer and 45 vol % of polypropylene as a non-degradable polymer under the conditions shown in the following Table 3. The prepared monofilament in the segmented pie form was warped with 120 yarns/7" beam to prepare the mesh according to the above warp knitted texture of Example 3. The prepared mesh was cured at 95° C. for 10 minutes. The properties of the mesh, such as thickness, weight, tensile strength, and stiffness were determined according to the conventional measuring methods, and the results are shown in the following Table 6.

Example 4

The mesh was prepared by the same method as in Example 1, except that the number of the segments of the non-degradable polymer was 8. The properties of the prepared mesh, such as thickness, weight, tensile strength, and stiffness were determined according to the conventional measuring methods, and the results are shown in the following Table 6.

Example 5

The mesh was prepared by the same method as in Example 1, except that the revolution speed (rpm) of the quantitative pump was 9.7 rpm for the polypropylene (50 vol %) and 4.9 rpm for the glycolide/caprolactone copolymer (50 vol %). The properties of the prepared mesh, such as thickness, weight, tensile strength, and stiffness were determined according to the conventional measuring methods, and the results are shown in the following Table 6.

Example 6

The mesh was prepared by the same method as in Example 1, except that the revolution speed (rpm) of the quantitative pump as 9.6 rpm for the polypropylene (40 vol %) and 7.2 rpm for the glycolide/caprolactone copolymer (60 vol %). The properties of the prepared mesh, such as

TABLE 3

| Polymer | polypropylene | Dioxanone (90)/trimethylenecarbonate (9)/caprolactone (1) tri-block copolymer |
|---|---|---|
| Melt index (g/10 min, 230° C.) | 10 | 10 |
| Spinning Conditions | | |
| Extruder | Ext. 1 | Ext. 2 |
| The number of segments of the non-degradable polymer | 6 | — |
| Pre-pump pressure (kgf/cm$^2$) | 80 | 80 |
| Temperature in Extruder (° C.) Zone 1 | 150 | 150 |
| Zone 2 | 160 | 155 |
| Zone 3 | 165 | 160 |
| Zone 4 | 165 | 160 |
| Zone 5 | 165 | 160 |
| Temperature in Manifold (° C.) | 170 | 165 |
| Temperature in Quantitative Pump (° C.) | 170 | 165 |
| Temperature in Nozzle Pack Die (° C.) | 175 | |
| Capacity of Quantitative Pump (cc/rev) | 0.3 | 0.6 |
| Revolution speed of Quantitative Pump (rpm) | 8.75 | 5.35 |
| Temperature in Cooling Bath (° C.) | 25 | |
| Drawing Conditions | | |
| First Roller velocity (m/min) | 5.8 | |
| First Drawing Oven Temperature (° C.) | 70 | |
| Second Roller velocity (m/min) | 45 | |
| Second Drawing Oven Temperature (° C.) | 100 | |
| Third Roller velocity (m/min) | 53 | |
| Third Drawing Oven Temperature (° C.) | 120 | |
| Fourth Roller velocity (m/min) | 42 | |
| Total Drawing Ratio | 7.24 | |
| Preparation Conditions of the Mesh | | |
| Warping Conditions | 120 yarns/7" beam | |
| Warp Knitted Texture | Warp Knitted Texture Example 3 | |
| Curing Conditions | 95° C., 10 minutes | | thickness, weight, tensile strength, and stiffness were determined according to the conventional measuring methods, and the results are shown in the following Table 6.

Comparative Example 1

The mesh was prepared by the same method as in Example 1, except that the revolution speed (rpm) of the quantitative pump was 4.9 rpm for the polypropylene (25 vol %) and 7.3 rpm for the glycolide/caprolactone copolymer (75 vol %). The obtained monofilament was a sea/island type of monofilament wherein the polypropylene component was surrounded by the glycolide/caprolactone copolymer component as shown in FIG. 3A.

Comparative Example 2

The mesh was prepared by the same method as in Example 1, except that the melt index of polypropylene was 27. The monofilament had the segmented pie structure, but the tensile strength of the monofilament was poorer than that of Example 1, and the segmented pie structure was not symmetrical (FIG. 3B).

Comparative Example 3

The mesh was prepared by the same method as in Example 1, except that the third roller velocity and the fourth roller velocity of the drawing conditions were made the same at 55 m/min such that no stress-relaxation was applied.

The intensity of the obtained monofilament in the segmented pie form was improved compared with that of Example 1, but strand separation of the two components occurred when preparing the mesh (FIG. 3C).

Comparative Example 4

The thickness, weight, tensile strength, and stiffness of a conventional mesh product (Prolene Hernia mesh, Ethicon Co.) consisting of only polypropylene monofilament were measured according to the conventional measuring methods. The results are shown in the following Table 6.

Comparative Example 5

The thickness, weight, tensile strength, and stiffness of a conventional mesh product (Vypro II Hernia mesh, Ethicon Co.) comprising a glycolide/lactide copolymer multifilament as a degradable component and a polypropylene monofilament as a non-degradable component were measured according to the conventional measuring methods. The results are shown in the following Table 6.

Experimental Example

The property measuring methods are summarized in the following Table 4.

TABLE 4

| Property | Measuring Methods and Apparatuses |
|---|---|
| Diameter, mm | EP Regulation, Diameter |
| Tensile strength, kgf | EP Regulation, tensile strength, Instron corporation |

The property measuring methods are described in the following Table 5.

After measuring the initial properties, the properties of the mesh, wherein the degradable component was completely degraded under accelerated conditions (80° C., 10 days in PBS, pH 7.4) and only the non-degradable component remained, were measured, to compare the properties before and after degradation.

TABLE 5

| Property | Measuring Methods and Apparatuses |
|---|---|
| Thickness (μm) | EP Regulation, Diameter |
| Weight (g/m²) | The weight of 10 cm × 10 cm mesh was converted on the basis of m². |
| Tensile Strength (Kgf/inch) | 1" × 6" mesh was sampled in the horizontal and vertical directions in preparing the warp knitted texture, and the tensile strength was measured by the tensile strength tester (Instron, 4204, U.S.SA.) wherein the sample was equipped with 50 mm tensile distance and tensed at 50 mm/min. |
| Stiffness (mgf) | The mesh was cut to a 1" × 1" size, to measure the stiffness by the stiffness tester (Gurley Precision Instrument, U.S.A.) after setting the load at 5 g and the position at 2. |

The measured properties of the mesh prepared in Examples 1 to 6 and Comparative Examples 4 to 5 are shown in the following Table 6.

TABLE 6

| | | | Examples | | | | | | Comparative Examples | |
|---|---|---|---|---|---|---|---|---|---|---|
| | | Property | 1 | 2 | 3 | 4 | 5 | 6 | 4 | 5 |
| Property of Fiber | | Diameter (μm) | 150 | 145 | 140 | 150 | 150 | 200 | 150 | 100~150 |
| | | Tensile Strength (Kgf) | 1 | 0.8 | 1.1 | 0.9 | 0.9 | 1.8 | 1 | 1~2 |
| Property of Mesh | Initial Property | Thickness (μm) | 550 | 540 | 540 | 550 | 550 | 600 | 600 | 650 |
| | | Weight (g/m²) | 64 | 62 | 60 | 64 | 64 | 80 | 85 | 88 |
| | | Tensile Strength (Kgf) Vertical | 20 | 18 | 21 | 18 | 20 | 22 | 26 | 20 |
| | | Tensile Strength (Kgf) Horizontal | 6 | 5 | 6 | 5 | 6 | 8 | 16 | 6 |
| | | Stiffness (mgf) Vertical | 22 | 19 | 24 | 18 | 20 | 24 | 28 | 18 |
| | | Stiffness (mgf) Horizontal | 10 | 9 | 12 | 9 | 10 | 11 | 25 | 10 |
| | Property after degradation | Thickness (μm) | 450 | 450 | 440 | 470 | 470 | 420 | 600 | 470 |
| | | Weight (g/m²) | 25 | 25 | 24 | 25 | 27 | 30 | 85 | 35 |
| | | Tensile Strength (Kgf) Vertical | 12 | 9 | 8 | 10 | 13 | 12 | 26 | 12 |
| | | Tensile Strength (Kgf) Horizontal | 5 | 4 | 4 | 4 | 5 | 6 | 16 | 4 |

TABLE 6-continued

|  |  | Examples | | | | | | Comparative Examples | |
| --- | --- | --- | --- | --- | --- | --- | --- | --- | --- |
| Property | | 1 | 2 | 3 | 4 | 5 | 6 | 4 | 5 |
| Stiffness (mgf) | Vertical | 2 | 2 | 2 | 1.5 | 2 | 2 | 28 | 9 |
|  | Horizontal | 1 | 0.8 | 0.5 | 0.5 | 1 | 0.5 | 25 | 2 |

As shown in Table 6, when comparing the properties of the mesh of Examples 1 to 6, wherein the mesh was prepared with the monofilament in the segmented pie form consisting of the degradable materials and the non-degradable materials, with those of Comparative Example 4 to 5, wherein the mesh was prepared with only the non-degradable monofilament or the mixture of the degradable multifilament and the non-degradable monofilament, it is known that the initial properties of the mesh of the present examples were equal to those of the comparative examples, and the remaining amount and the stiffness are relatively reduced compared thereto, to improve the biocompatibility and the flexibility of the present inventive mesh.

That is, in the case of the conventional hernia mesh prepared with the polypropylene monofilament as in Comparative Example 4, the initial strength and the stiffness were maintained even after a certain time, while in the case of the mesh prepared as in Example 1, the degradable material was degraded and the amount remaining in the body was reduced to at least 3 times lower than that of Comparative Example 4, and the stiffness was reduced by at least 10 times to alleviate misfeelings of the patient.

Further, when comparing Examples 1 to 6 with Comparative Example 5, it is known that in Examples 1 to 6, the initial amount and the remaining amount after degradation is low, and the stiffness is lowered three to four times, to remarkably improve the biocompatibility and the flexibility.

Comparative Example 1 is a case in which the content of polypropylene is 30 vol % or less, showing that the monofilament obtained by conjugated spinning does not have the segmented pie structure but rather has the sea/islands structure wherein the polypropylene component is surrounded by the glycolide/lactide copolymer component. When performing conjugated spinning of two components with a big difference in the melt indexes as in Comparative Example 2, the component with the low melt index pushes the component with the high melt index to one side at the distributing plate in the spinnerette, to generate the unequal segmented pie structure. Further, when applying no stress-relaxation at the last heating stage of the drawing step as in Comparative Example 3, the stress is present between the fibers of the two components with different thermal contractibilities, which generates the fiber separation phenomenon when impacted from the outside, especially when warping and knitting while preparing the mesh.

As aforementioned, the present invention provides a useful technique for preparing a mesh using a monofilament in a segmented pie structure obtained by conjugated spinning of a degradable polymer and a non-degradable polymer, to improve biocompatibility and flexibility.

What is claimed is:

1. A method of preparing a hernia mesh, comprising the steps of spinning, solidification, crystallization, and drawing to prepare a monofilament, and the steps of warping, knitting, and curing to prepare the hernia mesh, wherein:

the spinning step is performed by melting 30 to 70 vol % of a degradable polymer and 30 to 70 vol % of a non-degradable polymer, and conducting conjugated spinning to form a segmented pie structure;

the drawing step is performed by applying stress-relaxation to prepare the monofilament; and the curing step is performed at 90 to 160° C. for 1 to 30 minutes, and wherein the melt index of the degradable polymer is not lower than the melt index of the non-degradable polymer, and the difference between the melt indexes of the degradable polymer and the non-degradable polymer is 10 or less, wherein the non-degradable polymer is partitioned by the degradable polymer and the degradable polymer has a continuous form.

2. The method according to claim 1, wherein stress-relaxation of at least 10% is applied.

3. The method according to claim 1, wherein the degradable polymer is a homopolymer or copolymer comprising one or more monomers selected from the group consisting of glycolide, glycolic acid, lactide, lactic acid, caprolactone (ε-caprolactone), dioxanone (p-dioxanone), trimethylene carbonate, polyanhydride, and polyhydroxyalkanoate (PHA).

4. The method according to claim 3, wherein the degradable polymer is a glycolide/caprolactone copolymer or a dioxanone trimethylenecarbonate/caprolactone copolymer.

5. The method according to claim 1, wherein the non-degradable polymer is selected from the group consisting of polyolefins, polyamides, polyurethanes, and fluoropolymers.

6. The method according to claim 5, wherein the non-degradable polymer is polypropylene, or a copolymer of propylene and ethylene.

7. The method according to claim 1, wherein the non-degradable polymer is divided into at least four strands.

8. The method according to claim 1, wherein the diameter of the monofilament is 100 to 250 μm.

9. The method according to claim 1, wherein the stiffness of the degradable polymer after degradation is decreased at least 70% compared with that before degradation.

10. The method according to claim 1, wherein the structure of the mesh is a square, hexagonal, or network structure.

11. The method according to claim 1, wherein the mesh has a pore size of 0.1 to 4.0 mm and a thickness of 200 to 800 μm.

12. The method according to claim 1, wherein the mesh has a density of 8 to 20 gauges/inch based on the distance between the needles in a warp knitting machine.

13. The method according to claim 1, wherein the degradable polymer is partially dyed.

* * * * *